(12) United States Patent
Tonami et al.

(10) Patent No.: US 8,581,197 B2
(45) Date of Patent: Nov. 12, 2013

(54) RADIATION TOMOGRAPHY APPARATUS

(75) Inventors: Hiromichi Tonami, Kyoto-fu (JP); Masafumi Furuta, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 322 days.

(21) Appl. No.: 12/999,650

(22) PCT Filed: Jun. 17, 2008

(86) PCT No.: PCT/JP2008/061051
§ 371 (c)(1),
(2), (4) Date: Dec. 17, 2010

(87) PCT Pub. No.: WO2009/153860
PCT Pub. Date: Dec. 23, 2009

(65) Prior Publication Data
US 2011/0096897 A1    Apr. 28, 2011

(51) Int. Cl.
*G01T 1/161* (2006.01)
(52) U.S. Cl.
USPC .................................. 250/363.03; 250/515.1
(58) Field of Classification Search
CPC ....................................................... A61B 6/107
USPC ................................ 250/517.1, 515.1, 363.03
See application file for complete search history.

(56) References Cited

U.S. PATENT DOCUMENTS 5,451,789 A      9/1995   Wong et al.
5,825,031 A  *  10/1998   Wong et al. .............. 250/363.03

FOREIGN PATENT DOCUMENTS

| JP | 62177497 A * | 8/1987 |
| JP | 2004-533607 A | 11/2004 |
| JP | 3135182 U | 8/2007 |
| WO | WO-02/079802 A2 | 10/2002 |

OTHER PUBLICATIONS

International Search Report for the Application No. PCT/JP2006/061051 mailed Jul. 15, 2008.

* cited by examiner

*Primary Examiner* — Constantine Hannaher
(74) *Attorney, Agent, or Firm* — Cheng Law Group, PLLC

(57) ABSTRACT

Radiation tomography apparatus of this invention has a shield that shields entering of radiation flying from outside of the gantry. The shield is formed of shielding pieces. Consequently, there is no need for manufacturing the shield in a large and expensive furnace. Accordingly, the radiation tomography apparatus may be provided that is easily manufactured and achieves suppressed cost. Moreover, with the radiation tomography apparatus of this invention, maintenance may be performed through removal of the shielding pieces without removing the entire shield.

15 Claims, 13 Drawing Sheets

(a)

(b)

(a)

(b)

(c)

(a)

(b)

(a)

(b)

RADIATION TOMOGRAPHY APPARATUS

TECHNICAL FIELD

This invention relates to radiation tomography apparatus that images radiation. Particularly, this invention relates to radiation tomography apparatus provided with a group of radiation detectors having block radiation detectors arranged in a ring shape.

BACKGROUND ART

In medical fields, emission computed tomography (ECT: Emission Computed Tomography) apparatus is used that detects radiation (such as gamma rays) emitted from radiopharmaceutical that is administered to a subject and is localized to a site of interest for obtaining sectional images of the site of interest in the subject showing radiopharmaceutical distributions. Typical ECT apparatus includes, for example, a PET (Positron Emission Tomography) device and an SPECT (Single Photon Emission Computed Tomography) device.

A PET device will be described by way of example. The PET device has a group of radiation detectors having block radiation detectors arranged in an arc shape. The group of radiation detectors is provided for surrounding a subject, and allows detection of radiation that is transmitted through the subject.

Among PET devices, a PET-Mammography device (hereinafter, referred to as a PET-Mammo device) for conducting a breast cancer physical examination has a characteristic that more doses of radiation fly from outside of a gantry toward the apparatus in comparison with typical PET devices. Accordingly, the PET-Mammo device has a shield that shields entering of radiation flying from outside of the gantry. Description will be given of a configuration of a conventional PET-Mammo device. As shown in FIG. 14, the conventional PET-Mammo device 50 has a gantry 51 with an opening for introducing a site of interest B of a subject M, a group of radiation detectors 52 that is provided so as to surround the opening of the gantry 51 on an outer periphery thereof and detects radiation, and a ring-shaped shield 53 on one end of the group of radiation detectors 52 that is adjacent to the subject M.

It should be noted that, in the PET-Mammo device 50, a whole body of the subject M is not introduced into the opening of the gantry 51. Radiopharmaceutical is administered to the subject M by injection in advance for conducting diagnosis with the PET-Mammo device 50. The radiopharmaceutical is to be distributed over the whole body of the subject M. Specifically, radiation is emitted from the whole body of the subject M, and flies toward the group of radiation detectors 52 from not only the site of interest B inside the gantry but also a site other than the breast of the subject M. Radiation 54 derived from outside of the gantry is obstructive to imaging of radiopharmaceutical distributions in the site of interest B. Accordingly, in order to obtain a sectional image more suitable for diagnosis, the conventional mammo-PET apparatus 50 has a ring-shaped shield 53 on one end of the group of radiation 52 adjacent to the subject M that prevents radiation 54 derived from outside of the gantry from entering into the group of radiation detectors 52 (see, for example, Patent Literature 1.)

Patent Literature 1

U.S. Pat. No. 5,451,789

DISCLOSURE OF THE INVENTION

Problem to be Solved by the Invention

However, the conventional PET-Mammo device has the following problems. Specifically, one problem is that the conventional shield 53 is difficult for manufacturing. The shield 53 is composed of Tungsten, etc., with a high effective atomic number. The shield 53 is a sintered metal that is formed by heating powder up to a temperature close to a melting point. The Tungsten is a hard-to process material of high melting point and high hardness. Consequently, a large and expensive furnace is needed for forming the shield 53, which leads to difficulty in manufacturing the conventional shield 53.

Another problem is that the conventional shield 53 has a difficulty in assembling the PET-Mammo device 50. Since Tungsten is a metal of high density, the shield 53 has a considerable weight. Accordingly, a process of attaching the shield 53 inside the gantry is to be complicated upon manufacturing of the PET-Mammo device 50.

A further problem is that the configuration of the conventional shield 53 has a difficulty in maintenance of the PET-Mammo device 50. In the PET-Mammo device, it is necessary to replace a radiation detector that constitutes the group of radiation detectors 52 due to aged deterioration and the like. Here, an operation is required of removing the shield 53 once from the group of radiation detectors 52. Since the shield 53 is a member having a considerable weight as mentioned above, this operation is to be complicated. Accordingly, the conventional PET-Mammo device 50 needs high cost for maintenance.

This invention has been made regarding the state of the art noted above, and provides radiation tomography apparatus of low cost and easy maintainability that has divided shields for shielding radiation derived from outside of a gantry.

Means for Solving the Problem

This invention is configured as stated below in order to achieve the above object. Radiation tomography apparatus according to this invention includes a group of radiation detectors with radiation detectors for detecting radiation arranged at least in an arc shape, and a shield for shielding radiation that is provided so as to cover one plane side end of the group of radiation detectors, in which the shield is formed of two or more shielding pieces that are combined with one another, and the shielding pieces comprises a first shielding piece having a cut-out on a given side thereof; and a second shielding piece having a projection that contacts the first shielding piece and projects toward the cut-out, and the first shielding piece contacts the second shielding piece by fitting the cut-out and the projection.

[Operation and Effect]

With the configuration of this invention, the shield for shielding radiation is formed of two or more shielding pieces that are combined with one another. Consequently, the shield of this invention is easily manufactured. The shield of this invention is, for example, a sintered metal that is formed by heating powder with Tungsten as a main component up to a temperature close to a melting point. The configuration of this invention may be realized through manufacturing of the shielding pieces individually, and thereafter combining of them with one another. Consequently, there is no need for manufacturing the shield in a large and expensive furnace.

Accordingly, the radiation tomography apparatus may be provided that is easily manufactured and achieves suppressed cost.

The foregoing configuration may ensure contact of the first shielding piece and the second shielding piece adjacent to each other that constitute the shielding pieces for forming the shield. The cut-out of the first shielding piece and the projection of the second shielding piece fit with each other. Consequently, both shielding pieces contact, which avoids occurrence of a gap therebetween. Accordingly, radiation derived from outside of the gantry may surely be prevented from entering into the group of radiation detectors.

Moreover, this invention may realize easy assembly of the radiation tomography apparatus. The shield has a considerable weight. According to this invention, however, the shielding pieces may individually be incorporated into the radiation tomography apparatus, which results in easy assembly of the radiation tomography apparatus. Furthermore, this invention may realize easy maintenance to the radiation tomography apparatus. Specifically, with the configuration of this invention, maintenance may be performed through removal of the shielding pieces without removing the entire shield. Accordingly, there is no need for removing the shield of a considerable weight upon maintenance, which results in easy maintenance to the radiation tomography apparatus of this invention.

Moreover, it is more desirable that an adjacent radiation detector of with the foregoing group of radiation detectors that is arranged adjacent to the shield has the same number as the shielding piece, and that each of the shielding pieces is arranged so as to cover each of the adjacent radiation detectors, thereby forming the shield.

[Operation and Effect]

The foregoing configuration may further realize easy maintenance to the radiation tomography apparatus. Specifically, in the foregoing configuration, an adjacent radiation detector in the group of radiation detectors that is arranged adjacent to the shield has the same number as the shielding piece. Accordingly, upon pulling out of one of the radiation detectors of the group of radiation detectors, the shielding piece that covers the radiation detector may be removed. As a result, the shielding pieces are to be removed at the minimum upon maintenance to the radiation tomography apparatus, which results in easier maintenance to the radiation tomography apparatus.

Moreover, it is more desirable that a bottom plate is provide on the other side end opposite to one side end in the foregoing group of radiation detectors for supporting each of the radiation detectors that constitute the group of radiation detectors, the bottom plate has two or more struts provided thereon that extend towards the one side end of the group of radiation detectors, and each of the shielding pieces is fixedly supported on the struts.

[Operation and Effect]

With the foregoing configuration, the shielding pieces may be integrally fixed. Specifically, the shielding pieces are fixed on the bottom plate via two or more struts. As a result, with the foregoing configuration, each shielding piece is integrally fixed, which may realize formation of a more rugged shield.

Moreover, it is more desirable that the foregoing strut removably fixes each of the shielding pieces, and that, when the strut releases fixation of a third shielding piece, the third shielding piece may move in a direction away from a center of curvature of an arc portion in the group of radiation detectors and the third shielding piece may move forward and backward along a given direction, whereby removal and fitting of the third shielding piece from and with the shield, respectively, may be performed reversibly.

[Operation and Effect]

The foregoing configuration may realize easier maintenance to the radiation tomography apparatus. Specifically, upon releasing of fixation of the struts to the third shielding piece, the third shielding piece may move in the direction away from the center of curvature of the arc portion in the group of radiation detectors. Accordingly, the third shielding piece may move in a given direction to be removed from the shield. In addition, the third shielding piece may also move in a direction opposite to the given direction to fit with the shield. That is, the foregoing configuration may complete maintenance merely by insertion and pulling out of the third shielding piece. Consequently, easy maintenance may be realized to the radiation tomography apparatus.

Moreover, the shielding piece and strut in the foregoing configuration have a pin hole provided for determining a relative position to each other.

[Operation and Effect]

According to the foregoing configuration, the shielding piece and strut have the pin hole provided therein. Specifically, a pin passes through the pin hole, whereby the shielding piece and the strut may temporarily be joined to each other. Accordingly, upon fixation of the shielding piece and the strut via a crew, no shielding piece moves as the screw turns. That is, according to the foregoing configuration, the shielding piece and the strut are coupled to each other with no shift in the relative position thereof. Consequently, the shielding pieces that constitute the shield are regularly arranged, thereby forming the shield that prevents radiation derived from outside of the gantry from entering into the group of radiation detectors.

Moreover, the group of radiation detectors in the foregoing configuration may be of a C-shape.

[Operation and Effect]

The foregoing configuration may realize provision of the radiation tomography apparatus that ensures insertion of the site of interest in the subject into the opening of the gantry. Where this invention is applied to mammo-PET apparatus, an arm of the subject is obstructive to insertion of a breast of the subject into the opening of the gantry. According to the foregoing configuration, a recess may be formed for retracting the arm of the subject, which ensures insertion of the breast of the subject into the opening of the gantry. Consequently, the foregoing configuration may realize provision of the radiation tomography apparatus having the whole region of the breast of the subject as a field of view.

Moreover, the group of radiation detectors in the foregoing configuration may be of a circular ring shape.

[Operation and Effect]

The foregoing configuration may realize provision of the radiation tomography apparatus in which pair annihilation radiation emitted from the site of interest of the subject is positively detected. According to the foregoing configuration, a blind area may be reduced as much as possible where no radiation may be detected with the group of radiation detectors. Consequently, data may increase that is available for tomography in the radiation tomography apparatus.

Effect of the Invention

With the foregoing configuration, the radiation tomography apparatus may be provided having suppressed manufacturing cost. According to the configuration of this invention, the shielding pieces are individually manufactured, and thereafter, combined to constitute the shield for shielding radiation derived from outside of the gantry. Consequently, there is no need for manufacturing the shield in a large and expensive furnace. Furthermore, this invention may realize easy maintenance to the radiation tomography apparatus. Specifically, according to this invention, maintenance may be performed through removal of the shielding pieces without removing the entire shield. Accordingly, there is no need for removing the shield of a considerable weight upon maintenance, which results in easy maintenance to the radiation tomography apparatus of this invention.

Figure 1:
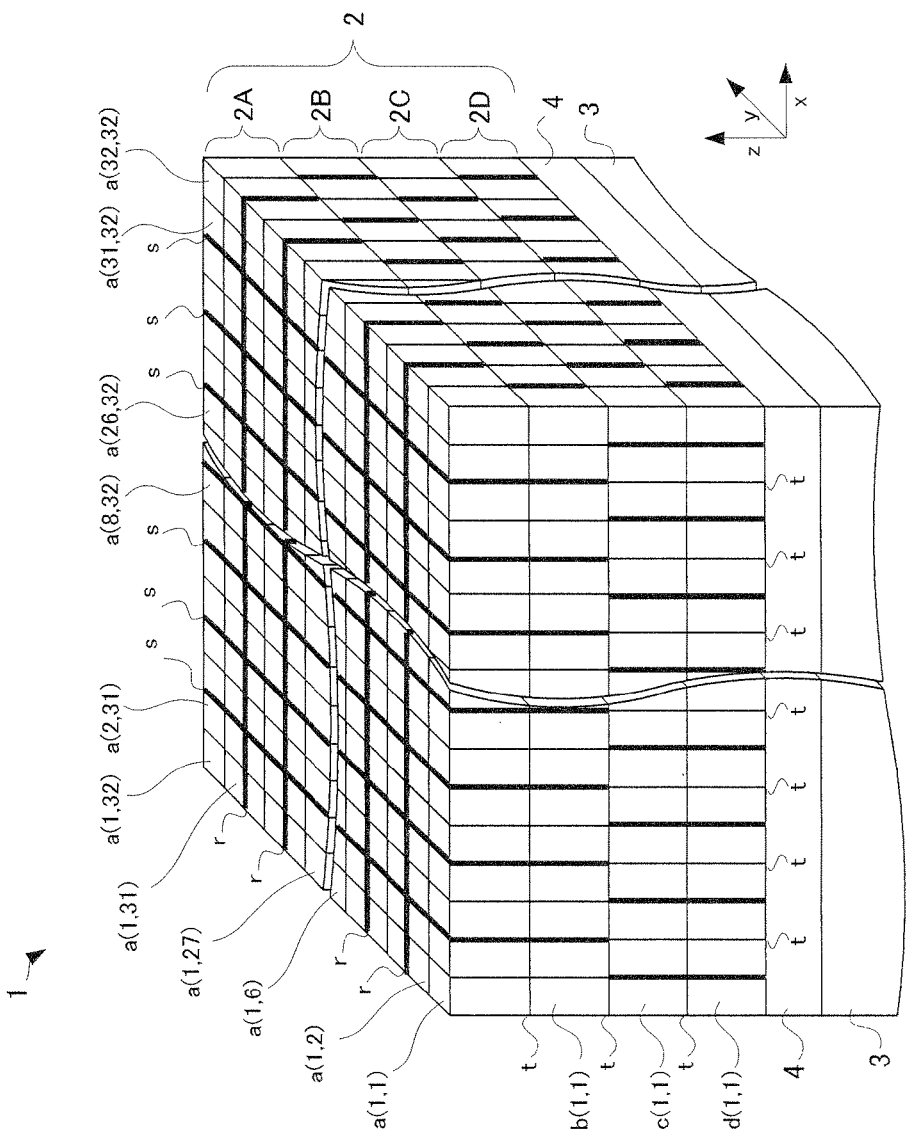
FIG. 1 is a perspective view of a radiation detector according to Embodiment 1.

DESCRIPTION OF REFERENCES 1 radiation detector
10 radiation tomography apparatus
12 fractured ring (group of radiation detectors)
13 shield
13a, 13b, 13c shielding piece
13e pin insertion hole (pin hole)
13f cut-out
13g projection
13p piece (first shielding piece)
13q piece (second shielding piece)
13r piece (third shielding piece)
14 bottom plate
21 first strut (strut)
22 second strut (strut)
22e pin hole

BEST MODE FOR CARRYING OUT THE INVENTION

Description will be given hereinafter of a configuration of radiation tomography apparatus according to one embodiment of this invention with reference to the drawings.

Embodiment 1

Firstly, prior to explanation of radiation tomography apparatus according to Embodiment 1, description will be given of a configuration of a radiation detector 1 according to Embodiment 1. FIG. 1 is a perspective view of the radiation detector according to Embodiment 1. As shown in FIG. 1, the radiation detector 1 according to Embodiment 1 includes a scintillator 2 that is formed of scintillation counter crystal layers each laminated in order of a scintillation counter crystal layer 2D, a scintillation counter crystal layer 2C, a scintillation counter crystal layer 2B, and a scintillation counter crystal layer 2A, in turn, in a z-direction, a photomultiplier tube (hereinafter referred to as a light detector) 3 having a function of position discrimination that is provided on an undersurface of the scintilla for 2 for detecting fluorescence emitted from the scintillator 2, and a light guide 4 interposed between the scintillator 2 and the light detector 3. Consequently, each of the scintillation counter crystal layers is laminated in a direction toward the light detector 3. Here, the scintillation counter crystal layer 2A corresponds to an incident surface of radiation in the scintillator 2. Each of the scintillation counter crystal layers 2A, 2B, 2C, and 2D is optically coupled, and includes a transparent material t between each of the layers. A thermosetting resin composed of a silicone resin may be used for the transparent material t. The scintillation counter crystal layer 2A corresponds to a receiver of the gamma rays emitted from a radioactive source. The scintillation counter crystals in a block shape are arranged in a two-dimensional array with thirty-two numbers of the scintillation counter crystals in an x-direction and thirty-two numbers of the scintillation counter crystals in a y-direction relative to a scintillation counter crystal a (1, 1). That is, the scintillation counter crystals from a (1, 1) to a (1, 32) are arranged in the y-direction to form a scintillator crystal array. Thirty-two numbers of the scintillator crystal arrays are arranged in the x-direction to form a scintillation counter crystal layer 2A. Here, as for the scintillation counter crystal layers 2B, 2C, and 2D, thirty-two numbers of the scintillator counter crystals are also arranged in the x-direction and the y-direction in a matrix in a two-dimensional array relative to a scintillation counter crystal b (1, 1), c (1, 1), and d (1, 1), respectively. In each of the scintillation counter crystal layers 2A, 2B, 2C, and 2D, the transparent material t is also provided between the scintillation counter crystals adjacent to each other. Consequently, each of the scintillation counter crystals is to be enclosed with the transparent material t. The transparent material t has a thickness around 25 μm. A gamma ray corresponds to radiation in this invention.

First reflectors r that extend in the x-direction and second reflectors s that extend in the y-direction are provided in the scintillation counter crystal layers 2A, 2B, 2C, and 2D provided in the scintillator 2. Both reflectors r and s are inserted in a gap between the arranged scintillation counter crystals.

The scintillator 2 has scintillation counter crystals suitable for detection of gamma rays in a three-dimensional array. That is, the scintillation counter crystal is composed of Ce-doped $Lu2_{(1-x)}Y_{2x}SiO_5$ (hereinafter referred to as LYSO.) Each of the scintillation counter crystals is, for example, a rectangular solid having a length of 1.45 mm in the x-direction, a width of 1.45 mm in the y-direction, and a height of 4.5 mm regardless of the scintillation counter crystal layer. The scintillator 2 has four side end faces that are covered with a reflective film not shown. The light detector 3 is multi-anode type, and allows position discrimination of incident fluorescence in the x and y.

Figure 2:
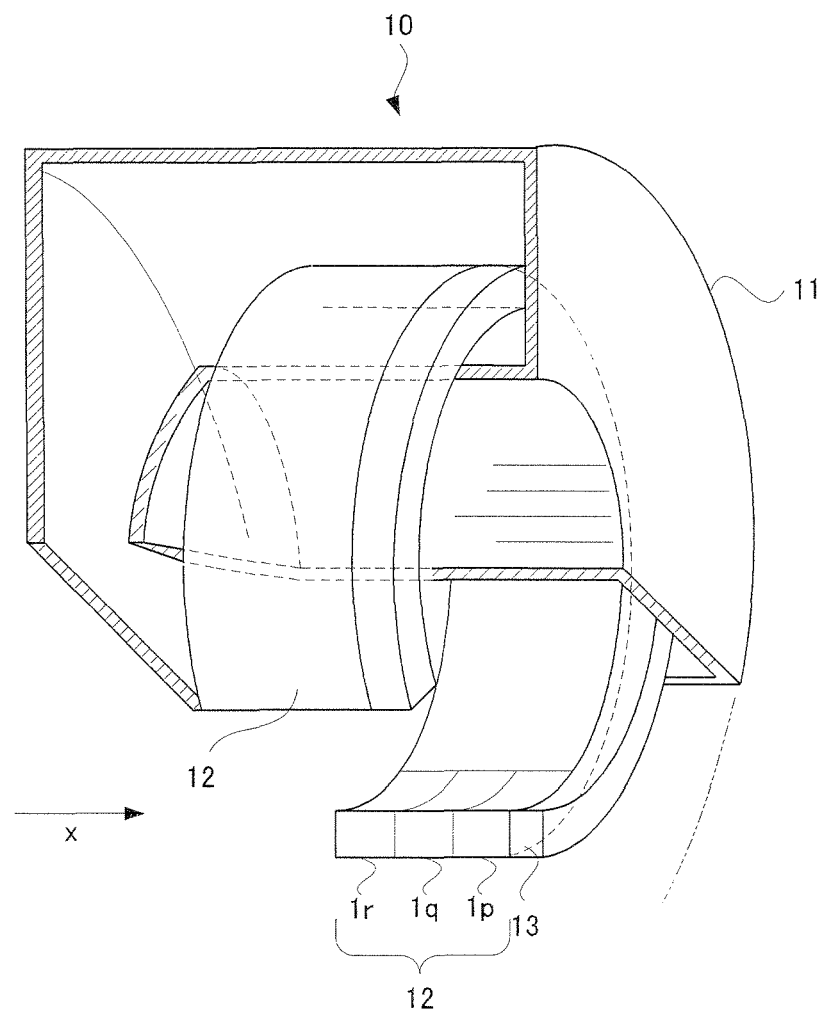
FIG. 2 is a partial sectional cut-away view showing a configuration of radiation tomography apparatus according to Embodiment 1.

Next, description will be given of a configuration of radiation tomography apparatus 10 according to Embodiment 1. FIG. 2 is a partial sectional cut-away view showing a configuration of the radiation tomography apparatus according to Embodiment 1. As shown in FIG. 2, the radiation tomography apparatus 10 according to Embodiment 1 has a gantry 11 having an opening for introducing a subject, and a fracture ring 12 in a C-shape that is provided inside the gantry 11 so as to contain the opening of the gantry 11. The fractured ring 12 has block radiation detectors 1p, 1q, 1r arranged in a C-shape. Gamma rays emitted from the subject enter into the fractured ring 12. The fractured ring 12 in the radiation tomography apparatus 10 determines intensity, an incidence period of time, and an incidence position of incident gamma rays. Here, the fractured ring corresponds to the group of radiation detectors in this invention. In addition, the gantry 11 according to Embodiment 1 has a C-shape following a contour of the fractured ring 12.

Moreover, the radiation tomography apparatus 10 according to Embodiment 1 has a C-shaped shield 13 that prevents radiation derived from the outside of the gantry 11 from entering into the fractured ring 12. The shield 13 is placed so as to cover one plane side end of the fractured ring 12. Specifically, the shield 13 is provided on one side end of a pair of plane side ends of the fractured ring 12 that is adjacent to the opening of the radiation tomography apparatus 10 for introducing a site of interest of a subject M. In other words, the shield 13 is provided such that the fractured ring 12 may extend in an axial direction. That is, the ring shield 13 separates a site other than the site of interest B of the subject M outside the gantry 11 and the fracture ring 12. Here, the shield 13 is, for example, composed of Tungsten.

Figure 3:
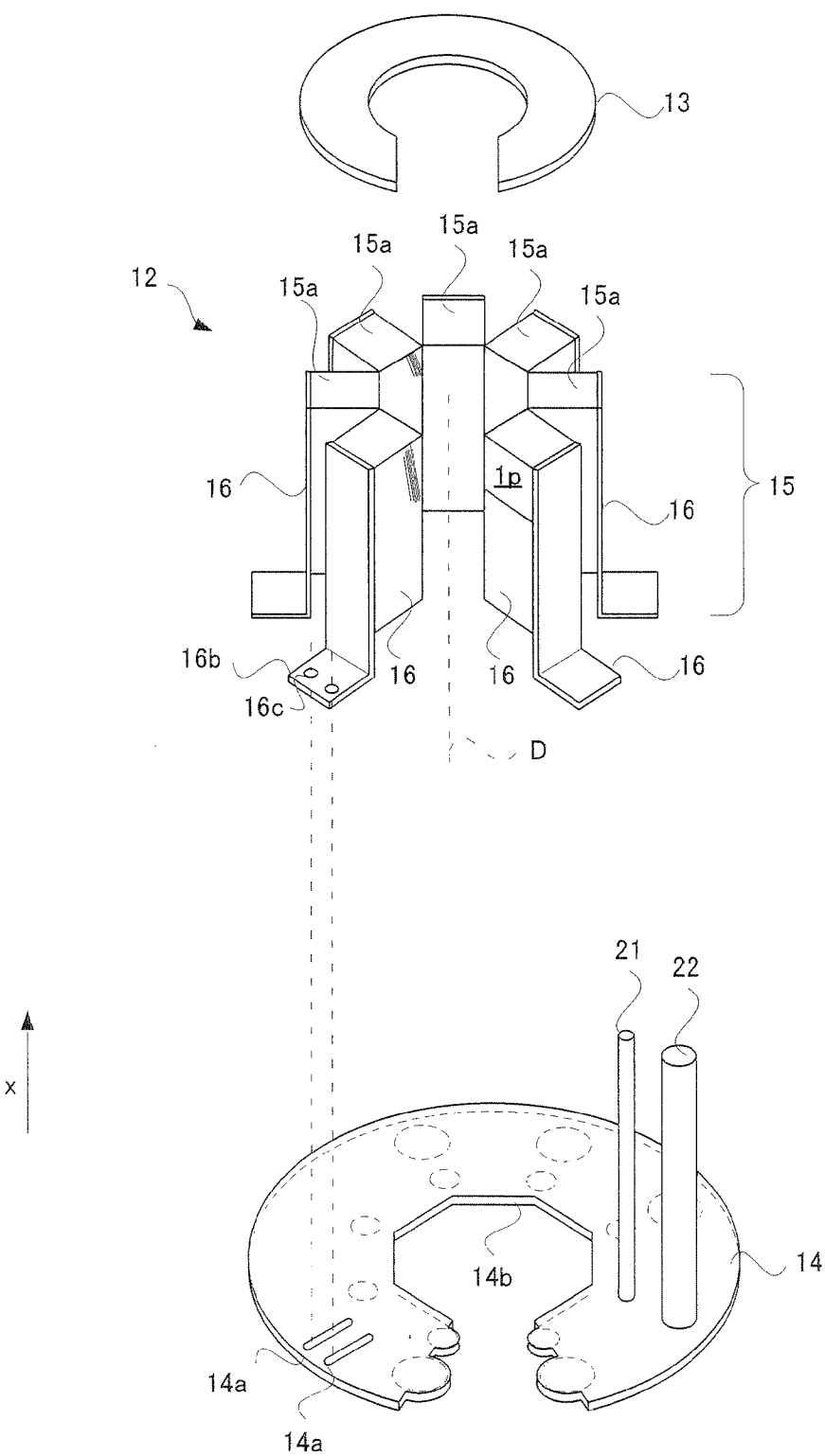
FIG. 3 is an exploded perspective view showing a configuration of a group of radiation detectors according to Embodiment 1.

Description will be given of a configuration of the fractured ring 12. FIG. 3 is an exploded perspective view showing a configuration of the group of radiation detectors according to Embodiment 1. As shown in FIG. 3, the fractured ring 12 has two or more detector units 15 arranged in an arc shape following the contour of the bottom plate 14 in the C-shape. Let a center of curvature of the arc be a center of curvature D. In the detector unit 15, a detector array 15a having three radiation detectors 1p, 1q, and 1r arranged in series in an x-direction and an L-shaped support tool 16 are coupled in a d-direction away from the center of curvature D in the fractured ring 12 (see FIG. 7.) Here, let a radiation detector closest to the shield 13 be a radiation detector 1p. The radiation detector 1p corresponds to the adjacent radiation detector of this invention that is arranged adjacent to the shield.

Seen the fractured ring 12 in the x-direction, the scintillators 2 provided in the detector unit 15 are arranged so as to face toward inside of the bottom plate 14. Accordingly, the scintillators 2 cover the inside of the fractured ring 12. In addition, the detector unit 15 is fastened to the bottom plate 14 via a sub-plate 16b, mentioned later, with a bolt and a nut. The sub plate 16b has a hole 16c provided therein through which a bolt passes. The bottom plate 14 has a long hole 14a for every detector unit 15 through which the bolt passes. Here in Embodiment 1, seven detector units 15 are arranged in the C-shape. The fractured ring 12 that extends from the bottom plate 14 in the x-direction has a C-shaped plane at a front end thereof that forms a front surface. The front surface is formed of seven radiation detectors 1p, and corresponds to one end of the group of radiation detectors of this invention.

The bottom plate 14 has an interior hole 14b provided in a center thereof. The interior hole 14b is octagonal, and each side thereof faces toward the detector unit 15. Moreover, the bottom plate 14 has eight first struts 21 and eight second struts 22 that extend in the x-direction for supporting the shield 13. The first struts 21 are arranged annularly so as to surround the interior hole 14b of the bottom plate 14. The second struts 22 are arranged annularly so as to surround a circular ring of the first struts 21 from outside thereof. Both struts 21 and 22 are provided within a V-shaped dead space of the bottom plate 14 that extends between the detector units 15 adjacent to each other. In addition, both struts 21 and 22 has a length in the x-direction approximately equal to that of the detector unit 15 in the x-direction that is provided on the bottom plate 14. Here, merely each one of both struts 21 and 22 is illustrated in FIG. 3. Actually, eight first struts 21 and eight second struts 22 are provided on the bottom plate 14.

Figure 4:
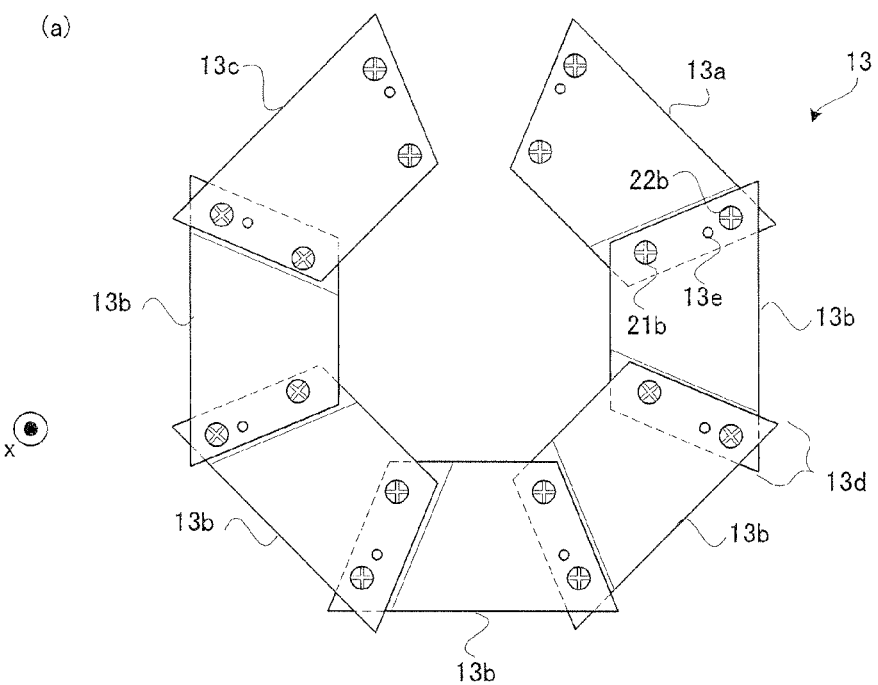
FIG. 4 is a plan view showing a configuration of a shield according to Embodiment 1.
Figure 4:
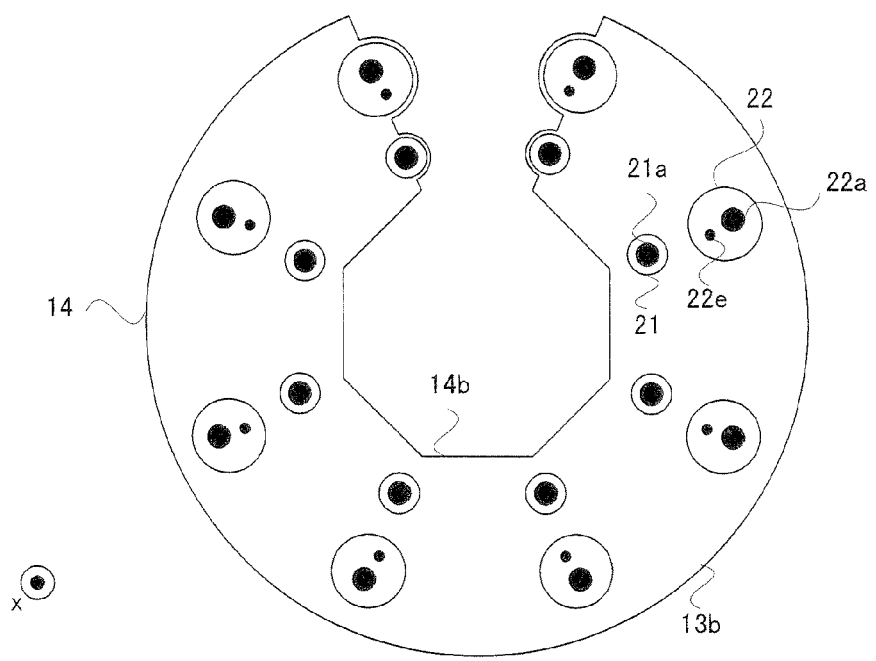

Description will be given of the shield 13. FIG. 4 is a plan view showing a configuration of the shield according to Embodiment 1. As shown in FIG. 4(a), the shield 13 is formed of seven shielding pieces 13a, 13b, 13c. The shielding piece 13a, 13b, 13c is a plate of a trapezoidal shape that is composed of Tungsten. The thickness thereof in the x-direction is set, for example, at 5 mm. In addition, a pair of shielding pieces 13a, 13b, and 13c adjacent to one another in the shield 13 partially overlap one another in the x-direction to form an overlap portion 13d. The shielding pieces 13a, 13b, and 13c each covers the front end of the single detector unit 15 in the x-direction, and are arranged in an arc shape seen as a whole thereof to form the C-shaped shield 13. Taking into consideration that one radiation detector 1p is provided on the front end of the detector unit 15 in the x-direction, the radiation tomography apparatus 10 has the shielding pieces 13a, 13b, and 13c of the same number (seven) as that of the radiation detectors 1p that constitute the front end surface of the fractured ring 12 in the x-direction.

Next, description will be given of both struts 21 and 22 for supporting the shield 13 provided on the bottom plate 14. As shown in FIG. 4(b), the first strut 21 has screw holes 21a provided therein for fixing the shielding pieces 13a, 13b, and 13c. Likewise, the second strut 22 has screw holes 22a provided therein for fixing the shielding pieces 13a, 13b, and 13c. As shown in FIG. 4(a), the overlap portion 13d has a screw 21b and a screw 22b provided therein that are used for collectively fixing a pair of shielding pieces 13a, 13b, and 13c overlapping thereon. The screw 21b and screw 22b are threaded into the foregoing screw hole 21a and screw hole 22a, respectively. Consequently, each of the side portions of the shielding pieces 13a, 13b, and 13c having a trapezoidal shape that are inclined to each other has a drilled hole 13k provided therein in the x-direction through which the screw 21b and the screw 22b pass (see FIG. 5.) Accordingly, seen one shielding piece 13a, 13b, and 13c, four drilled holes 13k are provided through which the screws 21b and 22b pass. In this way, one shielding piece 13a, 13b, 13c is supported with two first struts 21 and two second struts 22.

As shown in FIG. 4(b), the second strut 22 has a pin hole 22e provided therein through which an alignment pin, mentioned later, passes. The shielding piece 13a, 13b, 13c has a pin insertion hole 13e that extends in the x-direction through which the alignment pin (see FIG. 4(a)) passes. Taking into consideration that one shielding piece 13a, 13b, 13c is supported with two second struts 22, one pin insertion hole 13e is provided on each of the side portions of the shielding piece 13a, 13b, 13c having a trapezoidal shape that are inclined to each other. The pin insertion hole corresponds to the pin hole of this invention.

Figure 5:
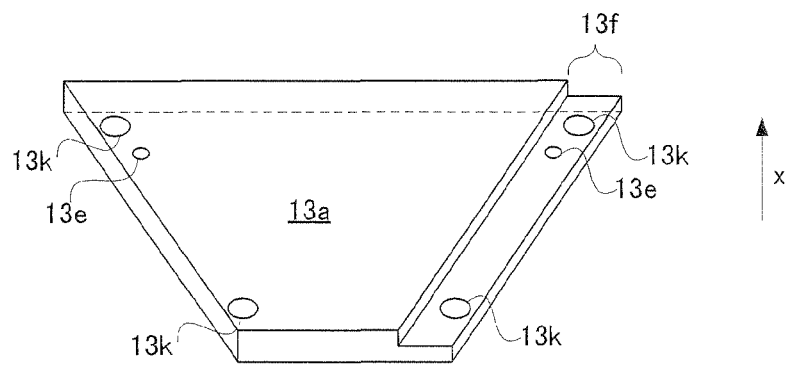
FIG. 5 is a perspective view showing a configuration of a shielding piece according to Embodiment 1.
Figure 5:
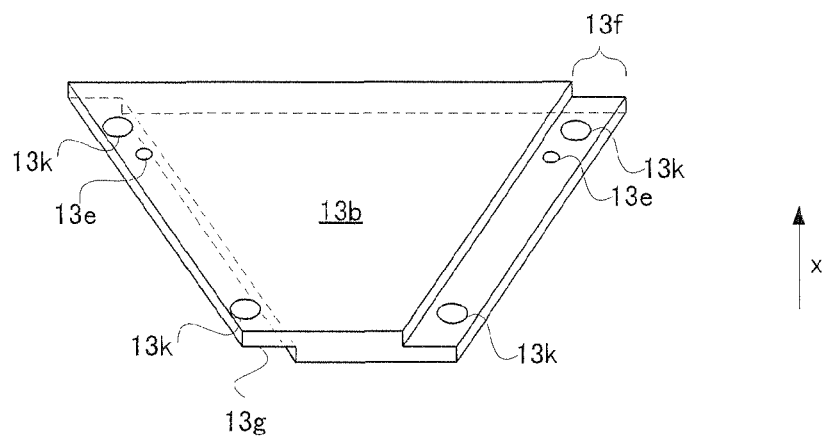
Figure 5:
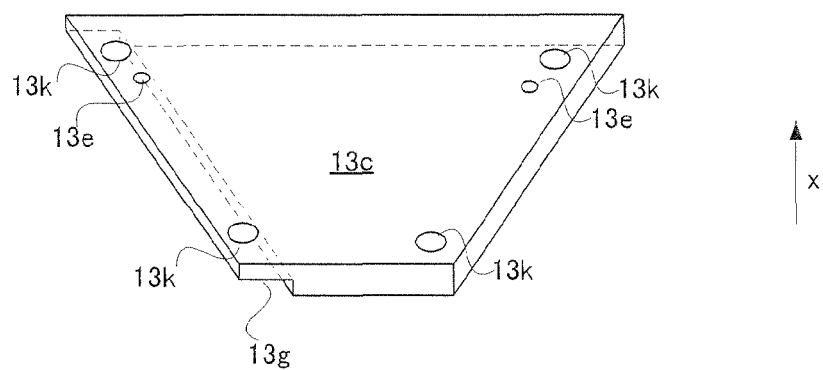

Description will be given in detail of the configuration of the shielding piece 13a, 13b, 13c. FIG. 5 is a perspective view showing the configuration of the shielding piece according to Embodiment 1. The shielding piece 13a, 13b, and 13c that constitutes the shield 13 has a first piece 13a, a second piece 13b, and a third piece 13c, respectively. The first piece 13a is located on one end side of the C-shaped shield 13. As shown in FIG. 5(a), a cut-out 13f is provided on one of the pair of side portions of the first piece 13a in the trapezoidal shape that are inclined to each other. Specifically, the cut-out 13f is provided so as to cut out an upper surface of the side portion in the first piece 13a. Here, one of the foregoing side portions corresponds to the given side with the cut-out of this invention.

As shown in FIG. 5(c), the shield 13 has on its other end the third piece 13c. A projection 13g is provided on one of the pair of side portions of the third piece 13c in the trapezoidal shape that are inclined to each other. Specifically, the projection 13g is provided so as to cover the upper surface of the side portion in the third piece 13c. Moreover, as shown in FIG. 5(b), the second piece 13b in a trapezoidal shape has any of the shielding pieces 13a, 13b, 13c adjacently placed on each of both the pair of side portions thereof inclined to each other. A cut-out 13f similar to that in the first piece 13a is provided on one of the pair of side portions of the second piece 13b, whereas a projection 13g similar to that in the third piece 13c is provided on the other thereof.

Figure 6:
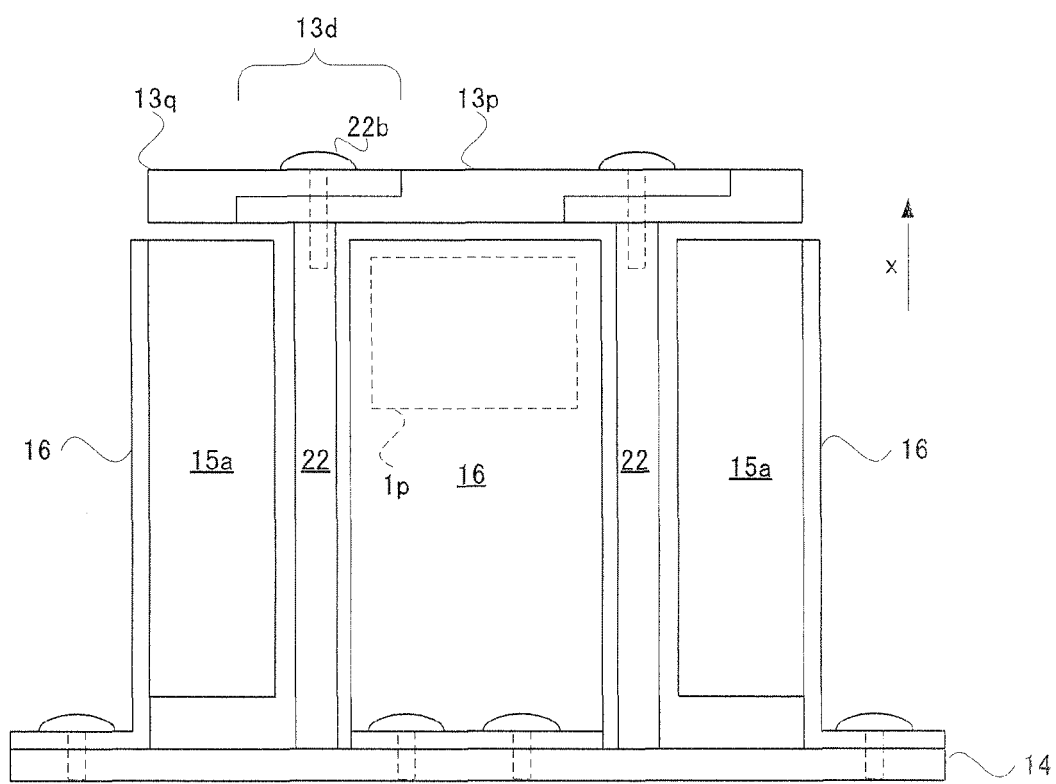
FIG. 6 is a plan view showing an overlap portion according to Embodiment 1.

FIG. 6 is a plan view showing an overlap portion according to Embodiment 1. As shown in FIG. 6, the piece 13p and the piece 13q adjacent thereto partially overlaps each other in the x-direction to form the overlap portion 13d. The overlap portion 13d has the cut-out 13f provided in the piece 13p and the projection 13g projecting toward the cut-out 13f provided in the piece 13p that fit with each other (see FIG. 5.) In this way, the piece 13p and the piece 13q contact to each other. Likewise, every overlap portion 13d of the shield 13 has the cut-out 13f and the projection 13g fitting with each other. Here, the piece 13p and the piece 13q correspond to the first shielding piece and the second shielding piece, respectively, in this invention.

Description will be next given of a configuration of the detector unit 15.

Figure 7:
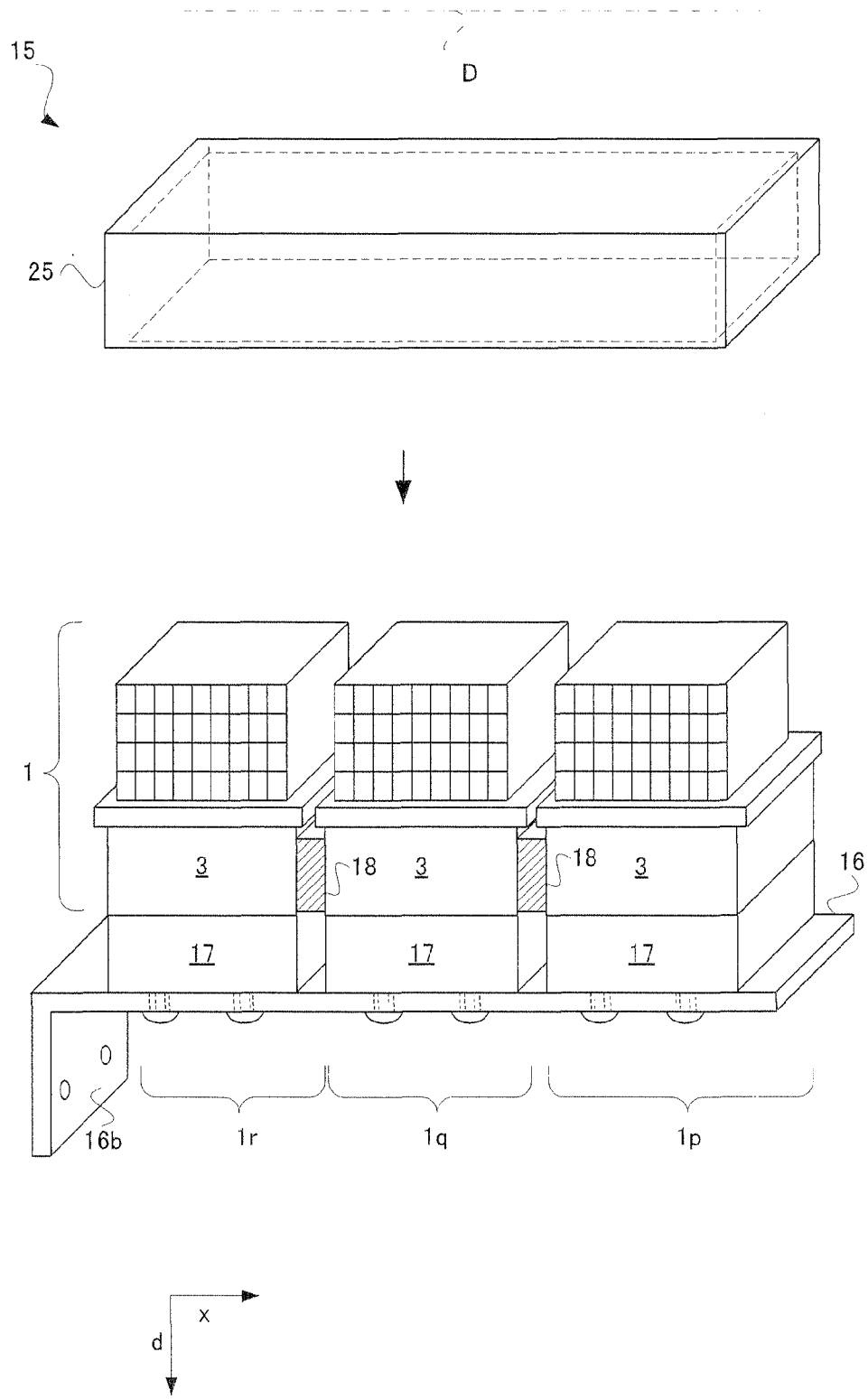
FIG. 7 is a plan view showing a configuration of a detector unit according to Embodiment 1.

FIG. 7 is a plan view showing a configuration of the detector unit according to Embodiment 1. As shown in FIG. 7, the detector unit 15 has three radiation detectors arranged in series in the x-direction. Specifically, the detector unit 15 has an L-shaped support tool 16, a bleeder unit 17 that is coupled to the support tool 16 in the d-direction by screw and provided with a bleeder circuit for supplying voltages to the radiation detector 1, and the radiation detector 1 that is connected to the bleeder unit 17 so as to extend in the d-direction. More specifically, the light detector 3 in the radiation detector 1 is connected to the bleeder unit 17. Such configuration allows the bleeder unit 17 to supply voltages directly to the light detector 3. Moreover, the detector unit 15 has three light detectors 3 that are joined via a plate spacer 18 in the x-direction. The scintillator 2 in FIG. 7 has nine scintillation counter crystals arranged in the x-direction. This is due to simplification of the drawing for suitable explanation. Actually, the scintillator 2 has thirty-two scintillation counter crystals arranged in the x-direction. Three scintillators 2 of the detector unit 15 are integrally covered with a box cover 25 made from aluminum, etc.

Easy maintenance may be realized to the radiation tomography apparatus 10 according to Embodiment 1. Next, description will be given of a maintenance method performed in the radiation tomography apparatus 10 when the radiation detector that constitutes the fractured ring 12 has to be replaced due to aged deterioration, etc.

<Shielding Piece Removal Step>

Figure 8:
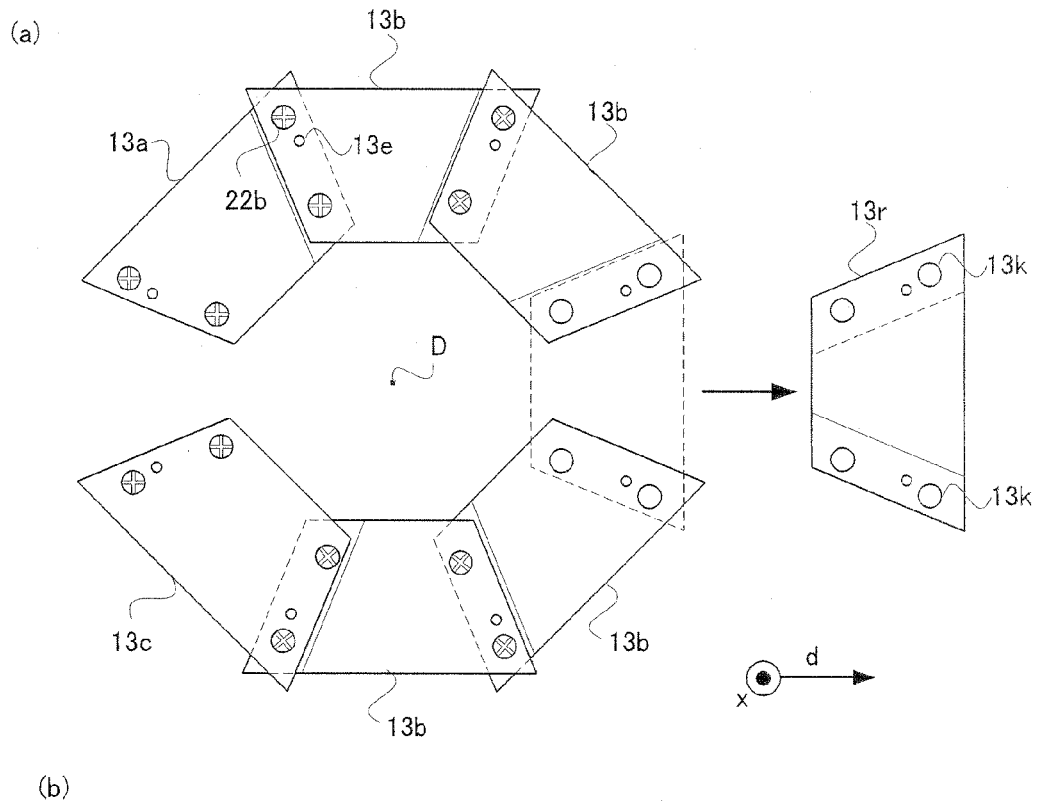
FIG. 8 is a plan view showing a step of removing the shielding piece according to Embodiment 1.
Figure 8:
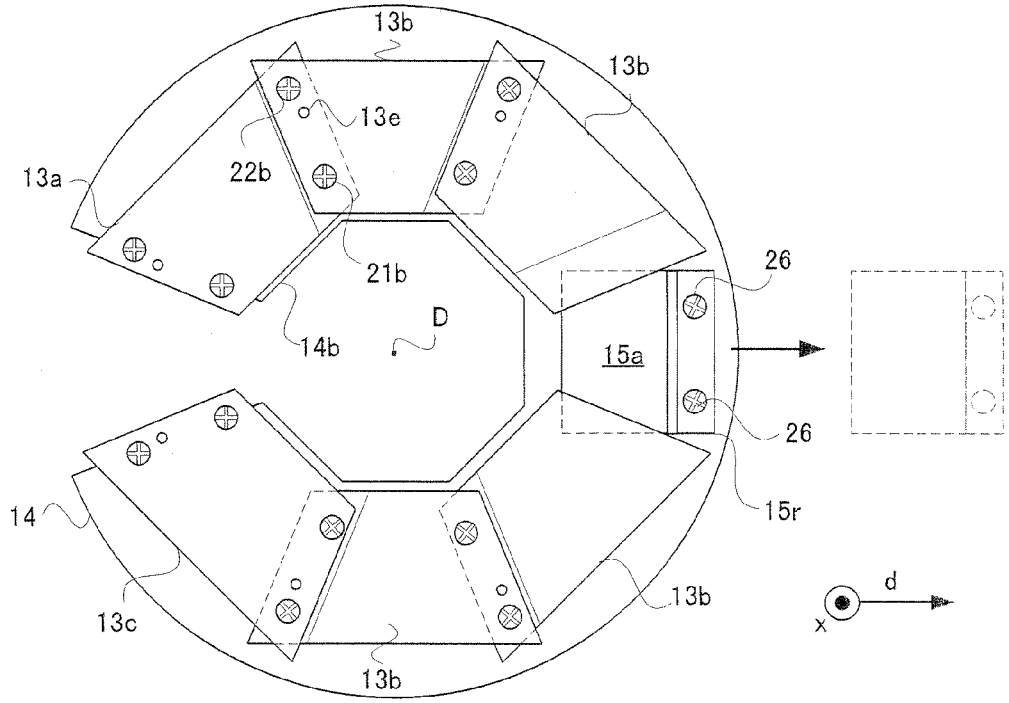

Upon replacement of the radiation detector that constitutes the fractured ring 12, it is necessary to remove a detector unit 15r of a damaged radiation detector from the fractured ring 12. Prior to this, the shielding piece 13a, 13b, 13c obstructive to this operation is removed from the shield 13. FIG. 8 is a plan view showing a step of removing the shielding piece according to Embodiment 1. It is assumed in FIG. 8(a) that the detector unit 15r to be replaced is covered with the piece 13r. Firstly, four screws 21b and 22b that fix the piece 13r (see FIG. 4) are threaded out and removed from the shield 13. Accordingly, the piece 13r may move in the d-direction away from the center of curvature D in the fractured ring 12. At this time, the piece 13r moves in the d-direction to be removed from the shield 13. Upon completion of the shielding piece removal step, the detector unit 15r is exposed as shown in FIG. 8(b) when seen the fractured ring 12 in the x-direction. Here, the piece 13r is one example of the third shielding piece of this invention.

<Detector Unit Replacement Step>

At this time, a bolt 26 for fixing the detector unit 15r to the bottom plate 14 is also exposed when seen the fractured ring 12 in the x-direction. In the detector unit replacement step, the bolt 26 is released to pull out the detector unit 15r in the d-direction. Instead, a new detector unit 15 is inserted into the fractured ring 12 by moving into a direction approaching to the center of curvature D in the fractured ring 12. Thereafter, the new detector unit 15 is fixed to the bottom plate 14 via the bolt 26. Thus, the step is to be completed.

<Shielding Piece Reattaching Step>

Figure 9:
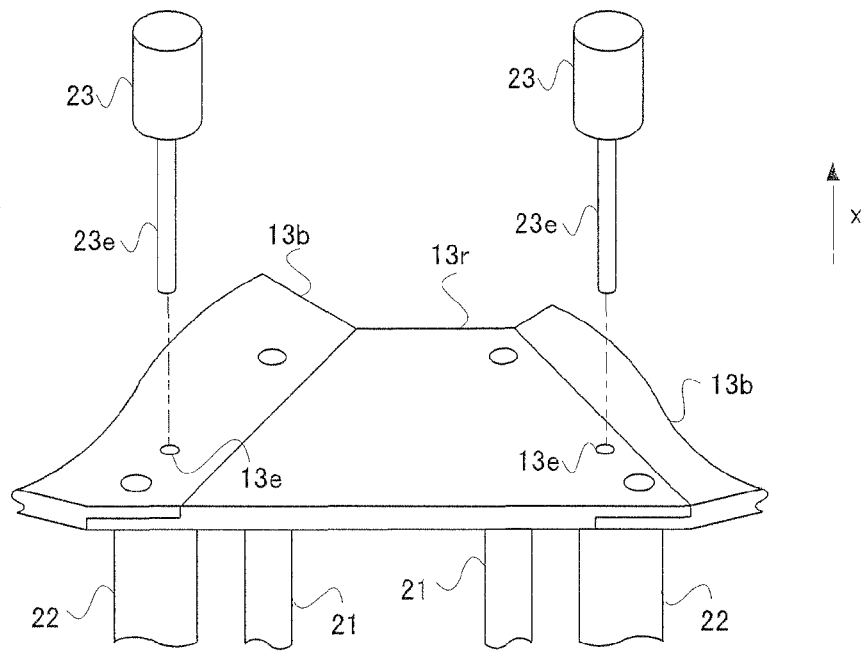
FIG. 9 is a perspective view showing a step of fitting the shielding pieces according to Embodiment 1.
Figure 9:
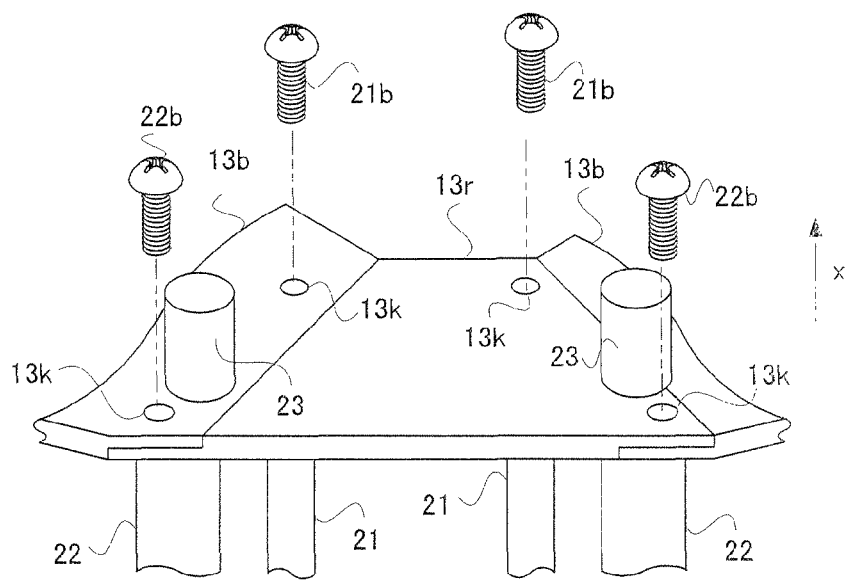

Subsequently, the piece 13r again fit with the shield 13 for reattaching thereof. FIG. 9 is a perspective view showing a step of fitting the shielding piece according to Embodiment 1. In this step, the piece 13r is fixed to both struts 21, 22 by screw. Prior to this, the piece 13r is aligned with respect to both struts 21, 22. Description will be given of the alignment. Firstly, the piece 13r is inserted in the direction approaching the center of curvature D in the fractured ring 12 (see FIG. 8), thereby fitting with the shield 13. Thereafter, as shown in FIG. 9(a), a pin 23e passes through each two pin insertion holes 13e provided in the piece 13r. Accordingly, a tip end of the pin 23e passes through the pin insertion hole 13e, and thereafter contacts the front end of the second strut 22. Then, a position of the piece 13r with respect to the second strut 22 is adjusted, and the tip end of the pin 23e fits into the pin hole 22e (see FIG. 4) provided in the second strut 22. In this way, the piece 13r is firstly aligned with respect to both struts 21, 22. Moreover, taking into consideration that the piece 13r has two pin insertion holes 13e provided therein, the piece 13r is temporarily joined to the second strut 22 via two pins 23e. Accordingly, once the piece 13r is aligned with respect to both struts 21, 22 through insertion of two pins 23e, the piece 13r does not shift with respect to both struts 21 and 22.

In addition, a proximal end of the pin 23e is connected to a base 23 having a larger diameter than the pin insertion hole 13e. Consequently, upon insertion of the pin 23e into the pin insertion hole 13e, the base 23 engages an outer periphery of the pin insertion hole 13e, which avoids further insertion of the pin 23e into the pin insertion hole 13e any more.

Then, as shown in FIG. 9(b), the screw 21b and the screw 22b pass through four drilled holes 13k provided in each of side portions of the trapezoidal piece 13r that are inclined to each other, thread into each of the screw holes 21a, 22a provided in both struts 21, 22 while the piece 13r is temporarily joined to the second strut 22 via two pins 23e. Consequently, the piece 13r is fixed to both struts 21, 22. In this way, maintenance to the radiation tomography apparatus 10 according to Embodiment 1 is to be completed.

The foregoing explanation on the maintenance exemplifies the case where the second piece 13b is to be removed. Where the first piece 13a or the third piece 13c is to be removed, similar maintenance as above is performed, and thus description thereof will be omitted. In addition, in the foregoing shielding piece removal step, the pins 23e may once pass through two pin insertion holes 13e in the piece 13c prior to removal of four screws 21b, 22, from the piece 13r. Consequently, the piece 13r is temporarily joined to the second strut 22 via two pins 23e, thereby being prevented from moving as the screws 21b, 22b turn.

Moreover, the piece 13r moves in the direction away from the center of curvature D in the fractured ring 12 (see FIG. 8), whereby removal and fitting of the piece 13r from and with the shield 13, respectively, may be performed reversibly.

Figure 10:
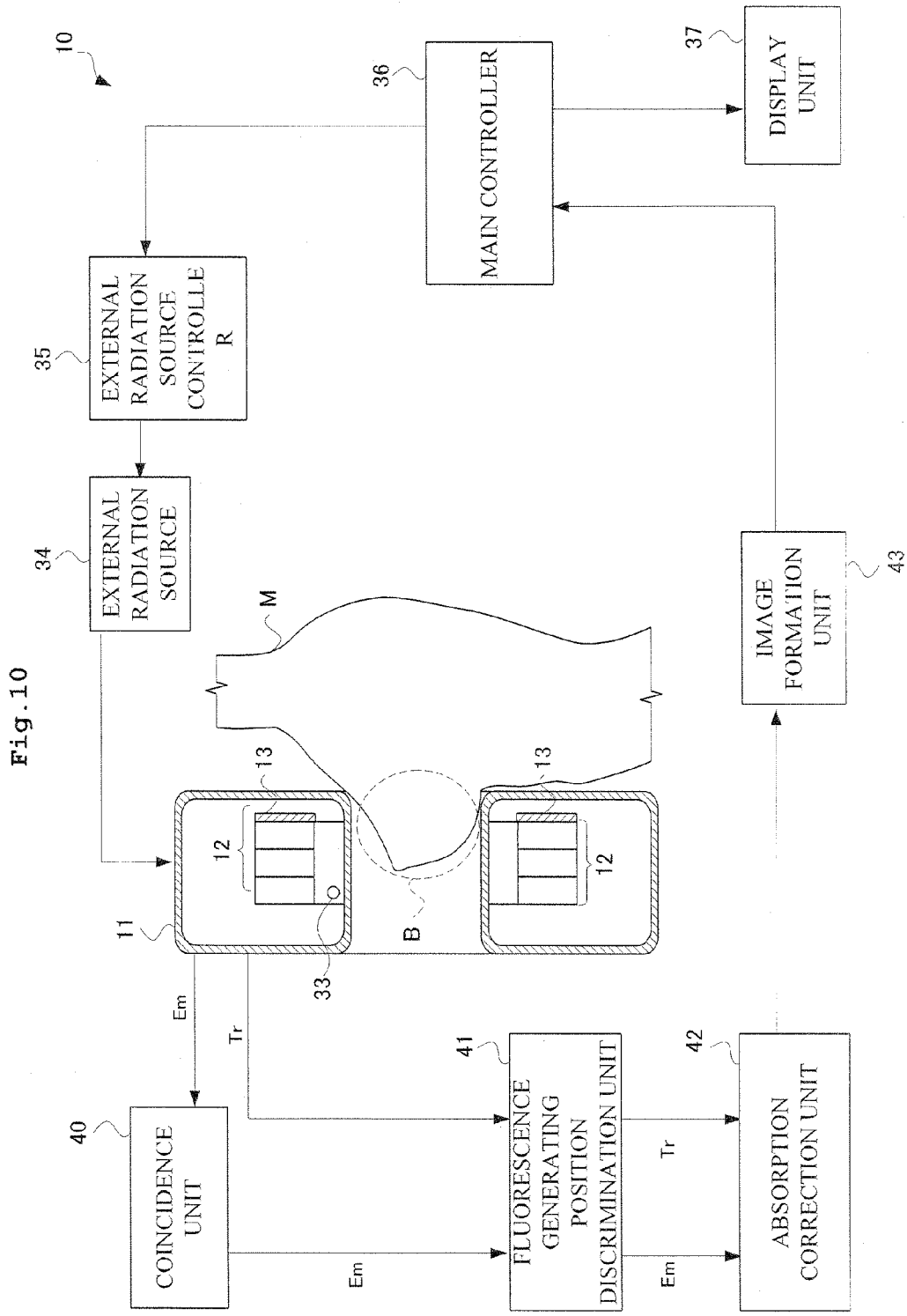
FIG. 10 is a functional block diagram showing a configuration of the radiation tomography apparatus according to Embodiment 1.

Next, description will be given of operations of the radiation tomography apparatus 10 according to Embodiment 1. FIG. 10 is a functional block diagram showing a configuration of the radiation tomography apparatus according to Embodiment 1. As shown in FIG. 10, the radiation tomography apparatus 10 according to Embodiment 1 has a gantry 11, a fractured ring 12 in a C-shape provided inside the gantry 11, a shield 13 in a C-shape that prevents radiation derived from outside the gantry 11 from entering into the fractured ring 12, an external radiation source 33 provided on an inner surface side of the fractured ring 12 for emitting fan beams of gamma rays, and an external radiation source drive 34 for driving thereof. Here, the external radiation source 34 is controlled under an external radiation source controller 35. The radiation tomography apparatus 10 further includes each unit for obtaining an sectional image on a site of interest B of a subject M. Specifically, the radiation tomography apparatus 10 includes a coincidence unit 40 to receive gamma ray detection signals showing a detection position, detection strength, and detection time of gamma rays from the fractured ring 12 for performing coincidence of an annihilation gamma ray-pair, a fluorescence generating position discrimination unit 41 to discriminate an incident position of gamma rays in the fractured ring 12 based on two pieces of gamma ray detection data determined to be an annihilation-gamma-rays pair in the coincidence unit 40, an absorption correction unit 42 to perform absorption correction of gamma rays with reference to transmission data mentioned later, and an image formation unit 43 to form a radiation tomography image on the site of interest B.

The radiation tomography apparatus 10 according to Embodiment 1 further includes a main controller 36 to control such as the external radiation source controller 35 en bloc, and a display unit 37 to display the radiation tomography image. The main controller 36 is formed of a CPU, and performs execution of various programs to realize the external radiation source controller 35 and coincidence unit 40, the fluorescence generating position discrimination unit 41, the absorption correction unit 42, and the image formation unit 43.

Description will be given to operations of the radiation tomography apparatus according to Embodiment 1 with reference to FIG. 10. Upon conducting of examinations with the radiation tomography apparatus 10 according to Embodiment 1, firstly the site of interest B (breast) of the subject M is inserted into the opening of the gantry 11 with radiopharmaceutical being administered thereto by injection in advance. Transmission data is obtained that shows absorption distributions of gamma rays within the site of interest B. Specifically, beams of gamma rays in a fan shape are applied from the external radiation source 33 towards the site of interest B. The gamma ray beams will pass through the site of interest B to be detected with the fractured ring 12. Such detection is performed throughout the periphery of the site of interest B while rotating the external radiation source 33 along an arc track on the inner surface of the fractured ring 12, whereby an absorption map of gamma rays throughout the site of interest B is obtained.

Following obtaining of the transmission data as mentioned above, emission data is obtained to detect the annihilation-gamma-rays pair that is emitted from the radiopharmaceutical localized in the site of interest B. Prior to this, the external radiation source 33 obstructive to emission data obtaining is moved in the axis direction of the fractured ring 12 for storage thereof into a radiation source shield not shown.

Thereafter, emission data is obtained. Specifically, the fractured ring 12 detects an annihilation gamma-rays pair that is emitted from inside of the site of interest B having a traveling opposite direction. Gamma-ray detection signals detected with the fractured ring 12 are sent to the coincidence unit 40. It is considered as one count only when two gamma ray photons are detected simultaneously in positions different to each other in the fractured ring 12, and then subsequent data processing may be performed. Thereafter, such emission data is repeatedly obtained, whereby emission data may be obtained having sufficient number of counts for imaging localization of the radiopharmaceutical within the site of interest B. Finally, the site of interest B of the subject M is retracted from the opening of the gantry 11. An examination is to be completed.

Next, description will be given of data processing in the radiation tomography apparatus according to Embodiment 1 with reference to FIG. 10.

Transmission detection data Tr and emission detection data Em outputted from the fractured ring 12 are sent to the fluorescence generating position discrimination unit 41 to identify which scintillation counter crystal has detected the data. Detection data sent from the multi-anode type optical detector 3 includes information on fluorescence intensity distributions that the optical detector 3 detected, and the fluorescence generating position discrimination unit 41 calculates a center of gravity of fluorescence from the data. Consequently, the fluorescence position is discriminated in x-, y-, and z-directions in FIG. 1. As mentioned above, transmission detection data and emission detection data including incident positions of gamma rays are formed and sent to the subsequent absorption correction unit 42.

The absorption correction unit 42 performs absorption corrections to the emission detection data Em for eliminating influences of the gamma ray absorption distributions in the of interest B superimposed on the emission detection data Em while referring to the transmission detection data Tr noted above. Thus, detection data showing radiopharmaceutical distributions in the site of interest B with more accuracy is sent to the image formation unit 43, and then a radiation tomography image is to be reconstructed. Finally, the display unit 37 displays the image.

Here, the fractured ring has a C-shape. The reason therefor is to be described. In order to obtain a sectional image more suitable for diagnosis, it is necessary to insert the site of interest B of the subject M more deeply into the opening of the gantry 11. Thus, it is more desirable to contact the arm of the subject M firmly to the gantry 11. Consequently, a recess for introducing the arm of the subject M is provided so as to expand the opening of the gantry 11, and therefore, the gantry 11 has a C-shape. No detector unit 15 may be provided in a portion of the fractured ring 12 that corresponds to the recess. Therefore, the group of radiation detectors having the arranged radiation detectors in Embodiment 1 is the C-shaped fractured ring 12.

As noted above, according to the configuration of Embodiment 1, the shield 13 for shielding radiation is formed of two or more shielding pieces 13a, 13b, 13c that are combined with one another. Consequently, the shield 13 of Embodiment 1 is easily manufactured. The shield 13 of Embodiment 1 is, for example, a sintered metal that is formed by heating powder with Tungsten as a main component up to a temperature close to a melting point. The configuration of Embodiment 1 may be realized through manufacturing of the shielding pieces 13a, 13b, 13c individually, and thereafter combining of them with one another. Consequently, there is no need for manufacturing the shield 13 in a large and expensive furnace. Accordingly, the radiation tomography apparatus 10 may be provided that is easily manufactured and achieves Suppressed cost.

Moreover, Embodiment 1 may realize easy assembly of the radiation tomography apparatus 10. The shield 13 has a considerable weight. According to Embodiment 1, however, the shielding piece 13a, 13b, 13c may individually be incorporated into the radiation tomography apparatus 10, which results in easy assembly of the radiation tomography apparatus 10. Furthermore, Embodiment 1 may realize easy maintenance to the radiation tomography apparatus 10. Specifically, according to Embodiment 1, maintenance may be performed through removal of the shielding pieces 13a, 13b, 13c without removing the entire shield 13. Accordingly, there is no need for removing the shield 13 of a considerable weight upon maintenance, which results in easy maintenance to the radiation tomography apparatus 10 of Embodiment 1.

This invention is not limited to the foregoing embodiments, but may be modified as follows.

(1) In the foregoing embodiment, the scintillation counter crystal is composed of LYSO. Alternatively, the scintillation counter crystal may be composed of another materials, such as GSO ($Gd_2SiO_5$), may be used in this invention. According to this modification, a method of manufacturing a radiation detector may be provide that allows provision of a radiation detector of low price.

(2) In the foregoing embodiment, the scintillator 2 has four scintillation counter crystal layers. This invention is not limited to this embodiment. For instance, the scintillator formed of one scintillation counter crystal layer may be applied to this invention. Moreover, the scintillation counter crystal layer may be freely adjusted in number depending on applications of the radiation detector.

(3) The fluorescence detector in the foregoing embodiment is formed of the photomultiplier tube. This invention is not limited to this embodiment. A photodiode or an avalanche photodiode, etc. may be used instead of the photomultiplier tube.

Figure 13:
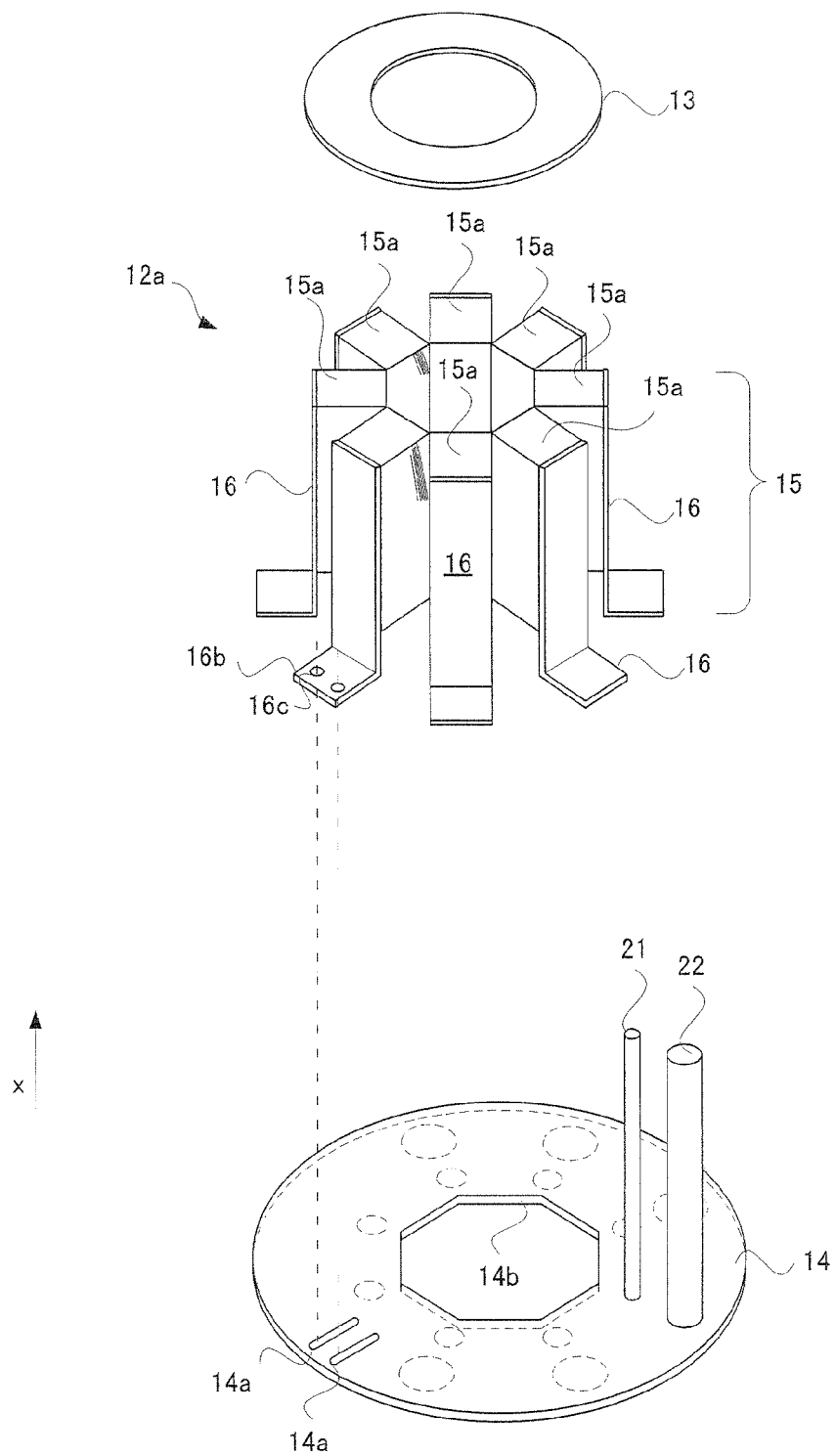
Figure 14:
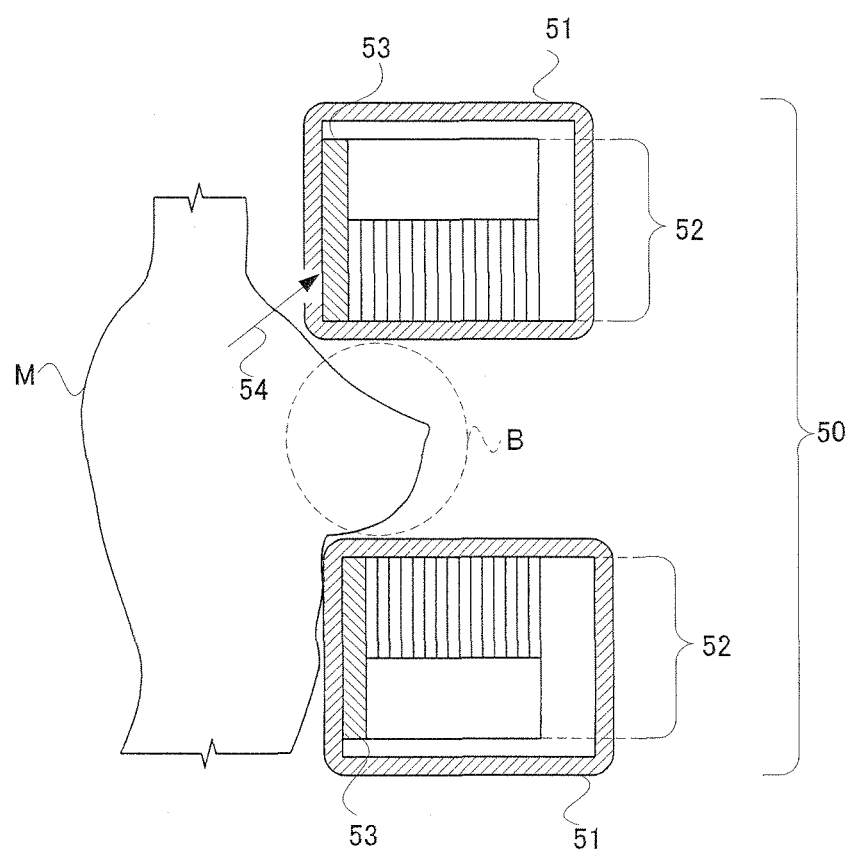
FIG. 14 is a sectional view showing a configuration of a conventional radiation tomography apparatus.

(4) In the foregoing embodiment, the fracture ring has a C-shape. A group of radiation detectors in a ring shape may be mounted instead. Specifically, as shown in FIG. 13, the shield 13 and the bottom plate 14 may have an O-shape, and instead of the fractured ring 12, a detector ring 12 may have detector units 15 arranged annularly. Here, the gantry 11 according to this modification has an O-ring shape so as to correspond to the shape of the detector ring 12a.

Figure 11:
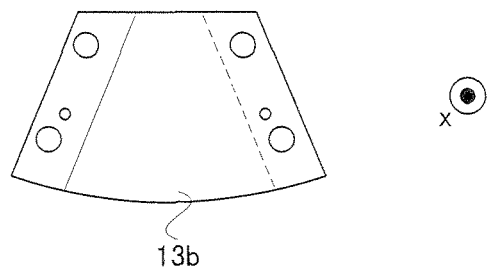
FIG. 11 is a plan view showing a configuration of one modification according to this invention.

(5) The shielding piece in the foregoing embodiment has a trapezoidal shape. This invention is not limited to this embodiment. As shown in FIG. 11, the shielding piece may have a fan shape.

Figure 12:
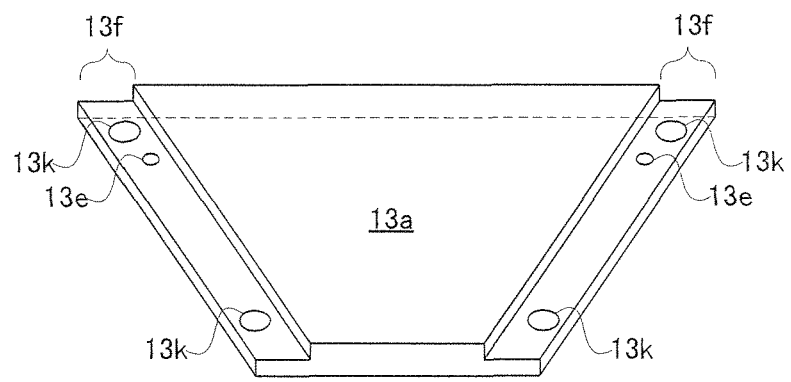
FIGS. 12 and 13 are perspective views each showing the configuration of one modification according to this invention.
Figure 12:
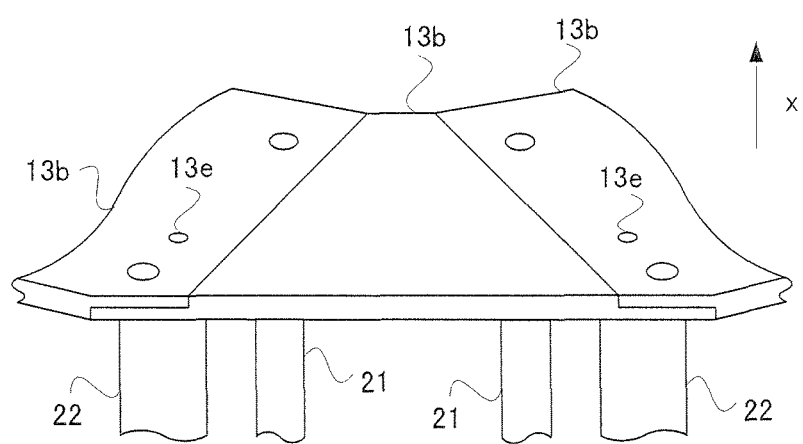

(6) In the foregoing embodiment, the second piece 13b has the cut-out and the projection. This invention is not limited to this embodiment. As shown in FIG. 12(a), the cut-out 13f is provided on each of side portions of the trapezoidal second piece 13b that are inclined to each other. According to the configuration, as shown in FIG. 12(b), the second adjacent pieces 13b are arranged in a C-shape while selecting both faces thereof so as to have an upside-down relation with respect to each other, thereby forming the shield 13.

(7) The fractured ring in the foregoing embodiment includes seven detector units. This invention is not limited to this embodiment. The detector unit that constitutes the fractured ring may be increased or decreased in number depending on applications of the radiation tomography apparatus. Accordingly, the shielding piece may also be increased or decreased in number that constitutes the shield.

INDUSTRIAL UTILITY

As described above, this invention is suitable radiation tomography apparatus for use in medical fields.

The invention claimed is:

1. Radiation tomography apparatus, comprising:
a group of radiation detectors with radiation detectors for detecting radiation arranged at least in an arc shape; and
a shield for shielding radiation that is provided so as to cover one plane side end of the group of radiation detectors,
the shield being firmed of two or more shielding pieces that are combined with one another, and
the shielding pieces comprises a first shielding piece having a cut-out on a given side thereof; and a second shielding piece having a projection that contacts the first shielding piece and projects toward the cut-out, and the first shielding piece contacts the second shielding piece by fitting the cut-out and the projection.

2. The radiation tomography apparatus according to claim 1, wherein
an adjacent radiation detector of the group of radiation detectors that is arranged adjacent to the shield has a same number as the shielding piece, and
each of the shielding pieces is arranged so as to cover each of the adjacent radiation detectors to form the shield.

3. The radiation tomography apparatus according to claim 2, wherein
a bottom plate is provided on the other side end opposite to one side end in the group of radiation detectors for supporting each of the radiation detectors that constitute the group of radiation detectors,
the bottom plate has two or more struts provided thereon that extend towards the one side end of the group of radiation detectors, and
each of the shielding pieces is fixedly supported on the struts.

4. The radiation tomography apparatus according to claim 2, wherein
the group of radiation detectors is of a C-shape.

5. The radiation tomography apparatus according to claim 2, wherein
the group of radiation detectors is of a circular ring shape.

6. The radiation tomography apparatus according to claim 1, wherein
a bottom plate is provided on the other side end opposite to one side end in the group of radiation detectors for supporting each of the radiation detectors that constitute the group of radiation detectors,
the bottom plate has two or more struts provided thereon that extend towards the one side end of the group of radiation detectors, and
each of the shielding pieces is fixedly supported on the struts.

7. The radiation tomography apparatus according to claim 6, wherein
the struts removably fix each of the shielding pieces, and
when fixation of a third shielding piece is released, the third shielding piece is movable in a direction away from a center of curvature of an arc portion in the group of radiation detectors, and the third shielding piece is movable forward and backward along a given direction, whereby removal and fitting of the third shielding piece from and with the shield, respectively, is performed reversibly.

8. The radiation tomography apparatus according to claim 7, wherein
each shielding piece and each strut have a pin hole provided for determining a relative position to each other.

9. The radiation tomography apparatus according to claim 7, wherein
the group of radiation detectors is of a C-shape.

10. The radiation tomography apparatus according to claim 7, wherein
the group of radiation detectors is of a circular ring shape.

11. The radiation tomography apparatus according to claim 6, wherein
each shielding piece and each strut have a pin hole provided for determining a relative position to each other.

12. The radiation tomography apparatus according to claim 6, wherein
the group of radiation detectors is of a C-shape.

13. The radiation tomography apparatus according to claim 6, wherein
the group of radiation detectors is of a circular ring shape.

14. The radiation tomography apparatus according to claim 1, wherein
the group of radiation detectors is of a C-shape.

15. The radiation tomography apparatus according to claim 1, wherein
the group of radiation detectors is of a circular ring shape.

* * * * *